(12) United States Patent
Negiz et al.

(10) Patent No.: US 8,026,194 B2
(45) Date of Patent: *Sep. 27, 2011

(54) LAYERED SPHERE CATALYST FORMULATIONS FOR SELECTIVE HYDROGENATION PERFORMANCE

(75) Inventors: Antoine Negiz, Wilmette, IL (US); Gregory J. Gajda, Mount Prospect, IL (US); Dean E. Rende, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 291 days.

This patent is subject to a terminal disclaimer.

(21) Appl. No.: 12/273,896

(22) Filed: Nov. 19, 2008

(65) Prior Publication Data

US 2010/0125037 A1 May 20, 2010

(51) Int. Cl.
*B01J 23/72* (2006.01)
(52) U.S. Cl. .......... 502/331; 423/326; 427/226
(58) Field of Classification Search .......... 502/331; 423/600, 610, 326, 439; 427/187, 226
See application file for complete search history.

(56) References Cited

U.S. PATENT DOCUMENTS

| | | | |
|---|---|---|---|
| 4,340,504 A * | 7/1982 | Courty et al. | 502/327 |
| 4,975,406 A * | 12/1990 | Frestad et al. | 502/302 |
| 5,464,802 A | 11/1995 | Gubitosa et al. | |
| 5,955,397 A | 9/1999 | Didillon et al. | |
| 6,005,148 A | 12/1999 | Tanielyan et al. | |
| 6,025,295 A | 2/2000 | Tanielyan et al. | |
| 6,177,381 B1 | 1/2001 | Jensen et al. | |
| 6,280,608 B1 | 8/2001 | Jensen et al. | |
| 6,417,419 B1 | 7/2002 | Abrevaya et al. | |
| 6,586,647 B1 | 7/2003 | Abrevaya et al. | |
| 6,627,578 B2 | 9/2003 | Xu et al. | |
| 6,797,669 B2 | 9/2004 | Zhang et al. | |
| 2003/0036476 A1 | 2/2003 | Arnold et al. | |
| 2003/0036669 A1 | 2/2003 | Ryu et al. | |
| 2005/0137434 A1 | 6/2005 | Li et al. | |
| 2006/0084830 A1 | 4/2006 | Ryu | |
| 2006/0266673 A1 | 11/2006 | Rende et al. | |
| 2006/0270865 A1 | 11/2006 | Wang et al. | |
| 2010/0125158 A1 | 5/2010 | Negiz | |

FOREIGN PATENT DOCUMENTS

| | | |
|---|---|---|
| JP | 54157507 (A) | 12/1979 |
| JP | 57185228 (A) | 11/1982 |
| RU | 2152252 | 7/2000 |

OTHER PUBLICATIONS

Guczi, L., Schay, Z., Stefler, S. Deganello, G., Liotta, L.F., and Venezia, A.M. Pumice-supported Cu-Pd catalysts: Journal of Catalysis 182: 456-462; 1999.

(Continued)

*Primary Examiner* — Stuart Hendrickson
*Assistant Examiner* — Richard M Rump
(74) *Attorney, Agent, or Firm* — Arthur E Gooding

(57) ABSTRACT

A catalyst for selective hydrogenation of hydrocarbons is presented. The catalyst selectively hydrogenates acetylenes and diolefins to increase the monoolefins in a product stream. The catalyst includes a layered structure with an inert inner core and an outer layer bonded to the inner core, where the outer layer is a metal oxide and has at least two metals deposited on the outer layer.

19 Claims, 8 Drawing Sheets

OTHER PUBLICATIONS

Furlong, Brian K., Alumina-supported palladium and palladium/copper catalysts Thesis 1996, Rice Digital Scholarship Archive, 1996.

Furlong, Brian K., Hightower, J.W., Chan, T.Y., Sarkany A, Guczi L. 1,3-Butadiene selective hydrogenation over pd/alumina; Applied Catalysis A: General 117:41-51; 1994.

Morreale, Bryan D. The Influence of H2S on Palladium and Palladium-Copper Alloy Membranes, Thesis 2006 Univ. of Pittsburg 2006.

Ordonez, Salvador, Hurtado Paloma, Sastre, Herminio and Diex, Fernando, Methane Catalytic Combustion over Pd/Al2O3; Applied Catalysis A: General 259: 41-48; 2004.

* cited by examiner

LAYERED SPHERE CATALYST FORMULATIONS FOR SELECTIVE HYDROGENATION PERFORMANCE

FIELD OF THE INVENTION

The invention relates to the selective hydrogenation of hydrocarbons. More specifically, the invention relates to of a catalyst to selectively hydrogenate C3-C11 diolefins and acetylenes in a hydrocarbon mixture to one or more respective C3-C11 monoolefins.

BACKGROUND OF THE INVENTION

Hydrocarbon stream feeds like pyrolysis gas feeds can have diene values ranging from 1-120 and diolefin weight percentages in such streams can range from 0.5 weight percent to 50 weight percent or above. Under an oxygen atmosphere diolefins are unstable. Diolefins present a challenge for processes involving catalysts because the diolefins are very reactive and polymerize even under hydrogen atmospheres at high temperatures forming gum. Because of the reactivity of diolefins catalysts that have poor activity are restricted in cycle length and have a propensity for polymerization because of the requirement for high temperatures. It is generally accepted at temperatures about 170° C. (338° F.) excess polymerization causes pressure drops across a catalytic reactor. These problems are generally worse if the catalyst comprises a porous active base such as gamma or theta alumina where polymerization of diolefins can cause swelling of the porous catalyst and can damage the structure of the catalyst.

In situations where the catalyst is an active catalyst there is a tendency for the active catalysts to convert diolefins and acetylenes as well as the monoolefins rapidly and often more selectively to their corresponding paraffins and naphthenes causing excess heat generation. Again, these conditions tend to favor gum formation and this is particularly so in a commercial application where a fixed bed adiabatic reactor is subjected to high temperature rises. The reactor's practical operating window is limited because of the pressure drop problems.

The current industrial practice for selectively hydrogenating diolefins or unsaturated hydrocarbon fractions is based on the use of sulfided nickel catalysts operating at moderately high temperatures of approximately 185° C. (365° F.). Sulfur loss from the catalyst to the product occurs and sulfur must be replenished to keep the catalyst active and operating optimally. Furthermore, once the sulfur is lost into the product, in some instances the sulfur must also be removed from the product and this adds another level of processing.

Other types of selective hydrogenation processes are also known, such as that described in JP54157507A. JP 54157507A describes the use of a palladium catalyst on an alumina support to selectively hydrogenate acetylene and methyl acetylene(alkynes) that are present in olefin fractions obtained in petrochemical processes. The catalyst described in JP54157507A comprises a thin alumina coating over an alpha alumina carrier of spherical or cylindrical shape and being around 1-20 mm in size, length and diameter. The alumina precursor, which can be aluminum nitrate, aluminum chloride, aluminum hydroxide and the like, is coated onto the alpha alumina carrier and then the coated alpha alumina carrier and alumina precursor is heat treated at between 400° C. (752° F.) to 700° C. (1292° F.) to create a thin alumina coating over the alpha alumina carrier. A palladium compound such as palladium chloride, palladium nitrate, and the like is dissolved in a suitable solvent, and then applied to the alumina coating to give effectively an enriched surface coating containing palladium. JP54157507A describes the use of the resulting catalyst in the selective hydrogenation of acetylene in a composition comprising ethylene.

US 2003/0036476 A1 describes a coated catalyst having a core and a shell surrounding the core, the core is made up of an inert support material. The shell is made up of a porous support substance, and the shell is physically attached to the core. A catalytically active metal selected from the group consisting of the metals of the 10th and 11th groups of the Periodic Table of the Elements is present in finely divided form in the shell. The coated catalyst is described as being suitable for the selective reduction of unsaturated hydrocarbons, specifically lower C2-C4 unsaturated hydrocarbons.

U.S. Pat. No. 6,177,381 B1, which is incorporated by reference in its entirety, describes a layered catalyst composition showing improved durability and selectivity for dehydrogenating hydrocarbons, a process for preparing the catalyst and processes for using the composition. The catalyst composition comprises an inner core such as alpha-alumina, and an outer layer bonded to the inner core composed of an outer non-refractory inorganic oxide such as gamma-alumina. The outer layer has uniformly dispersed thereon a platinum group metal such as platinum and a promoter metal such as tin. The composition also contains a modifier metal such as lithium. The catalyst composition is prepared by using an organic binding agent such as polyvinyl alcohol which increases the bond between the outer layer and the inner core. The catalyst composition is described as also being suitable for use in dehydrogenation and hydrogenation processes. Likewise, U.S. Pat. No. 6,280,608 B1 also describes a layered catalyst suitable for use in dehydrogenation and hydrogenation processes, while U.S. Pat. No. 6,486,370 B1 is directed to a layered catalyst suitable for use in dehydrogenation processes.

US 2006/0266673 A1 and US 2006/0270865 A1 describe a similar layered catalyst, but with an additional fibrous component in the outer layer. The fiber-containing layered catalyst is described as being suitable for use in dehydrogenation and hydrogenation processes including selective hydrogenation of dienes and trienes.

Improvements in selective hydrogenation is very important for reducing waste and recycle, thereby saving energy and material in the process. Improvements have a significant economic impact on the production of olefins.

SUMMARY OF THE INVENTION

The present invention provides for a new catalyst that improves the selective hydrogenation of diolefins and acetylenes. The catalyst comprises a layered structure, having an inner core made of an inert material, and an outer layer bonded to the inner core. The outer layer is a metal oxide selected from one or more of gamma alumina, delta alumina, eta alumina, theta alumina, silica-alumina, zeolites, non-zeolitic molecular sieves, titania and zirconia. The catalyst further includes a first metal deposited on the outer layer. The first metal is deposited on the outer layer in an amount such that the atomic ratio of the first metal to the aluminum in the outer layer is between 0.0001 and 0.1. The catalyst further includes a second metal deposited on the outer layer. The first metal is one or more metals selected from IUPAC Group 8-10 metals, and the second metal is one or more metals selected from IUPAC Group 11-17 metals.

In a specific embodiment, the catalyst comprises a composition such that the atomic ratio of the second metal to the first metal is less than 6.

Additional objects, embodiments and details of this invention can be obtained from the following drawings and detailed description of the invention.

DETAILED DESCRIPTION OF THE INVENTION

Figure 1:
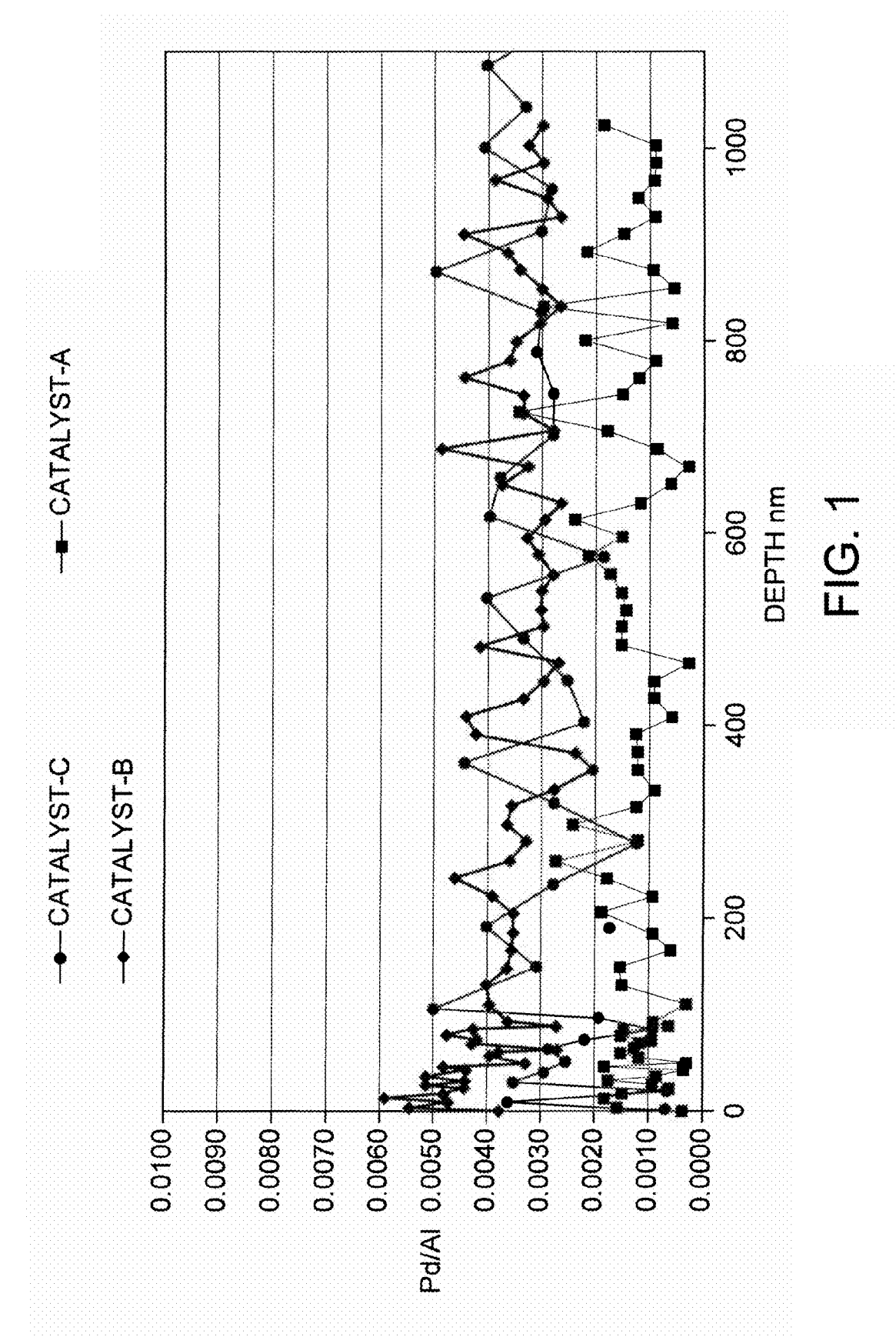
FIG. 1 is a plot of the palladium to aluminum atomic ratio profile in the outer layer as a function of distance in nanometers from the surface of the catalyst.

The present invention relates to a layered catalyst, and the use of the catalyst to selectively hydrogenate C3-C11 diolefins and acetylenes to C3-C11 monoolefins, which helps to mitigate some of the above mentioned limitations. The layered catalyst composition comprises an IUPAC Group 8-10 metal and an IUPAC Group 11-17 metal on a layered composition support. The support comprises an inner core of an inorganic oxide, which is preferably a refractory inorganic oxide, such as, without limitation, cordierite, and an outer layer of a non-refractory inorganic oxide, such as, without limitation, gamma alumina.

The product and process disclosed herein has been developed to enable one to selectively hydrogenate C3-C11 diolefins and acetylenes to C3-C11 monoolefins at relatively high space velocities using a layered catalyst that eliminates the need to use a sulfided nickel catalyst. This eliminates the need for associated sulfur addition due to loss of sulfur from the catalyst, and in some instances the subsequent removal of sulfur from the product as sulfur loss from the catalyst is lost into the product.

In particular, the catalyst comprises a layered structure having an inner core made of an inert material, and an outer layer bonded to the inner core. The outer layer comprises a metal oxide selected from gamma alumina, delta alumina, eta alumina, theta alumina, silica-alumina, zeolites, nonzeolitic molecular sieves, titania, zirconia, and mixtures of these oxides. The outer layer includes a first metal deposited on the outer layer where the first metal is one or more metals selected from IUPAC Group 8-10 metals. The outer layer further includes a second metal deposited on the outer layer where the second metal is one or more metals selected from IUPAC Group 11-17 metals, and where the first and second metals are deposited in amounts such that the atomic ratio of the first metal to the aluminum in the outer layer is between 0.0001 and 0.1. It is preferred that the atomic ratio of the first metal to the aluminum in the outer layer is between 0.001 and 0.005.

The layered structure of the catalyst comprises an inner core wherein the inner core is a solid material comprising one or more of the following materials: cordierite, mullite, olivine, zirconia, spinel, kyanite, aluminas, silicas, aluminates, silicates, titania, nitrides, carbides, borosilicates, boria, aluminum silicates, magnesia, fosterite, kaolin, kaolinite, montmorillonite, saponite, bentonite, clays that have little or low acidic activity, gamma alumina, delta alumina, eta alumina, and theta alumina. The inner core has an effective diameter of between 0.05 mm and 10 mm. By effective diameter is meant, for non-spherical shapes, the diameter that the shaped particle would have if it were molded into a sphere. In a preferred embodiment, the dried shaped particles are substantially spherical in shape. The outer layer is deposited on and bonded to the inner core to an effective thickness between 1 and 200 micrometers. A preferred outer layer thickness is between 20 and 70 micrometers.

In one embodiment, the outer layer comprises alumina. Preferred aluminas include gamma-alumina, theta-alumina, and silica-alumina. In referring silica-alumina, it should be noted that the term silica-alumina does not mean a physical mixture of silica and alumina but means an amorphous material that has been cogelled or coprecipitated.

In a preferred embodiment, the first metal is either palladium (Pd) or platinum (Pt), and the second metal is copper (Cu), silver (Ag), gold (Au), tin (Sn), germanium (Ge), lead (Pb), or a mixture of the second metals. The atomic ratio of the metals in the outer, or active, layer is important for the performance of the catalyst. If is preferred that the atomic ratio of the second metal to the first metal be less than 6, with a more preferred atomic ratio of less than 3, and a most preferred ratio of less than 1.5.

In one embodiment, the catalyst further includes a third metal deposited on the outer layer. The third metal is one or more metals selected from IUPAC Group 1-2 metals. In a preferred embodiment, the third metal is either potassium (K), lithium (Li), or a mixture of potassium and lithium.

In another embodiment, the catalyst further comprises a modifier metal deposited on the outer layer. The modifier metal is one or more metals selected from IUPAC Group 6-7 metals. Preferred modifier metals include molybdenum (Mo), tungsten (W), or rhenium (Re).

An example catalyst of the present invention is one that is preferred to comprise a layered structure having an inner core of an inert material and an outer layer bonded to the inner core with the outer layer comprising an alumina. The inner core is formed to have an effective diameter between 0.05 mm and 10 mm, with the outer layer having an effective thickness between 1 and 200 micrometers. The catalyst further comprises palladium deposited on the outer layer and copper deposited on the outer layer. The palladium is deposited in an amount such that the palladium to aluminum atomic ratio is between 0.001 and 0.005. The copper is deposited in an amount such that the atomic ratio of copper to palladium is less than 6, and preferably less than 1.5.

The catalyst of the present invention is for the selective hydrogenation of hydrocarbon streams having diolefins and/or acetylenes. The hydrocarbons are in the C3 to C11 range, and the hydrogenation process converts the diolefins and acetylenes to monoolefins in the C3 to C11 range. The hydrocarbon stream is contacted with the layered catalyst as described above at selected hydrogenation conditions in a hydrogenation reactor.

Selective hydrogenation conditions include operation of the hydrogenation reactor at a temperature between 30° C. and 300° C. The operation includes running the process under a hydrogen atmosphere, or a partial hydrogen atmosphere with an inert diluent. The reaction is carried out at a hydrogen to diolefin and acetylene molar ratio between 1:1 and 10:1, or with a hydrogen to total liquid feed molar ratio between 0.1:1 and 20:1. The selective hydrogenation furthermore can take place in a complete liquid or gas phase or in a mixture of the two phases. The temperature and pressure can be adjusted to operate between bubble and dew points of the reactive mixture.

The process converts between 30% and 100% of the diolefins and acetylenes to monoolefins. In a preferred operation, the process converts light ends of the hydrocarbon stream, in particular, the C3 components, or methyl acetylene and propadiene. The methyl acetylene and propadiene are converted to propylene for enhancing propylene production from processes that generate methyl acetylene and propadiene. The diolefin conversion can be completed in one reactor vessel or in multiple vessels that can be connected in series or in parallel. The diolefin content can be at least 5 ppm by wt.

Experiments:

The layered sphere catalyst was studied for performance in improving the selective hydrogenation of lower molecular weight hydrocarbons, and in particular acetylenes and dienes. The effects studied include the effects of the atomic ratios of the first metal, palladium, to the aluminum, and the atomic ratios of the first metal, palladium, to the second metal, copper, in the active layer on the catalyst performance. These are mainly characterized by XPS profiling. The experiments were performed using methyl acetylene (MA) and propadiene (PD), or MAPD, over the catalyst for selective hydrogenation to propylene.

From the experiments, a Pd:Al ratio between 0.001 and 0.005 in the active layer appeared to give optimum performance for the palladium metal. This ratio can change for a metal oxide other than alumina. The second metal to first metal ratio was found to give the best performance when the atomic ratio was less then 3 and preferably less than 1.5. The first metal in the experiments was palladium, and the second metal used was copper, silver, or gold.

These formulations were robust in that they were recoverable from organic upsets, or from $H_2S$ sulfur upsets.

Several catalysts were made and used with Pd and Cu in the outer, or active, layer. A first catalyst, Catalyst A, comprised a layered sphere with an inner core of cordierite with a 3 mm diameter, and a 50 micrometer outer layer of γ-alumina ($Al_2O_3$). The metals deposited on the outer layer were 0.02 wt % Pd, 0.038 wt % Cu, and 0.33 wt % K on the bulk basis. The theoretical CtL/Pd molar ratio is 3 based on the bulk ICP, and the theoretical Pd/Al atomic ratio in the layer is 0.001. The catalyst was prepared with long evaporation procedure with acid.

A second catalyst, Catalyst B, comprised the same makeup as catalyst A, except the preparation was with a short evaporation time.

A third catalyst, Catalyst C, comprised a layered sphere with an inner core of cordierite with a 3 mm diameter, and a 25 micrometer outer layer of γ-alumina ($Al_2O_3$). The metals deposited on the outer layer were 0.02 wt % Pd, 0.012 wt % Cu, and 0.33 wt % K on the bulk basis. The theoretical Cu/Pd molar ratio is 1 based on the bulk ICP, and the theoretical Pd/Al atomic ratio in the layer is 0.002. The catalyst was prepared with long evaporation procedure with acid.

The theoretical calculation of Pd:Al atomic ratio for a layered sphere catalyst having a 3 mm core and a 50 micrometer outer layer of γ-alumina, and with a 200 wt. ppm Pd loading comprises the following calculation. On a 100 gm catalyst basis, the layer weight of 10.2 grams for 100 grams of catalyst as measured, the moles of Pd=0.02/106.4=0.000188; and the grams of Al=10.2*(2*26.98)/101.06=5.4, which translates to moles of Al=5.4/26.98=2. The mole, or atomic, ratio of Pd:Al=0.00094 or approximately 0.001.

For a zirconia ($ZrO_2$) case, with a layered sphere catalyst having a 3 mm core and a 25 micrometer zirconia layer base, the wt. % zirconia layer is 12 wt %. On a 100 gm catalyst basis, the grams of Zr=12*91.22/(91.22+2*16)=8.8836; and the moles of Zr=8.8836/91.22=0.9738. For the same Pd loading of 0.02 wt %, the Pd:Zr atomic ratio=(moles of Pd/moles of Zr)=0.000188/0.09738=0.00193, or approximately 0.002. This is almost twice the Pd:Al ratio calculation above.

The distribution of Pd on the outer layer is shown in FIG. 1 by the Pd:Al ratio profiles taken with XPS sputtering. Catalyst A, as expected, shows a measured Pd:Al ratio of between 0.001 and 0.002. Catalyst B has twice the ratio of Catalyst A, showing more surface enrichment of Pd in the outer layer. Catalyst C had a layer thickness set at 25 micrometers, and as a result Catalyst B and Catalyst C have similar Pd:Al ratios, but Catalyst C has a more uniform Pd profile due to the long evaporation procedure.

Figure 2:
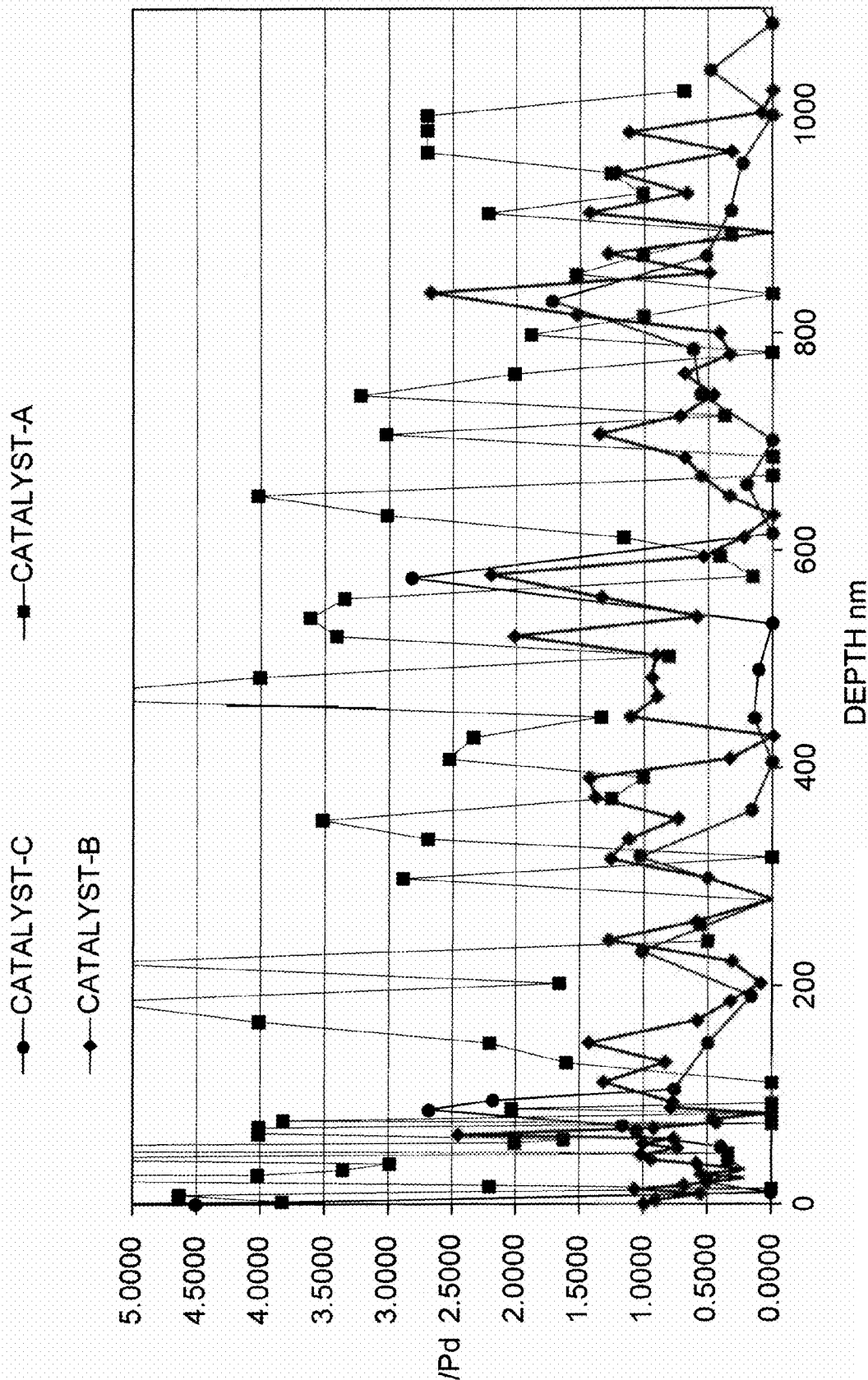
FIG. 2 is a plot of the copper to palladium atomic ratio profile in the outer layer as a function of distance in nanometers from the surface of the catalyst.

The distribution of the second metal to first metal, or Cu:Pd ratios, is shown in FIG. 2. Catalyst A has a high Cu:Pd ratio of around 3, as intended. Catalyst B, due to surface enrichment of the Pd has a Cu:Pd ratio of around 1. Catalyst C, as designed after Catalyst B, achieves the same Cu:Pd ratio of around 1, but with a more uniform profile.

Figure 3:
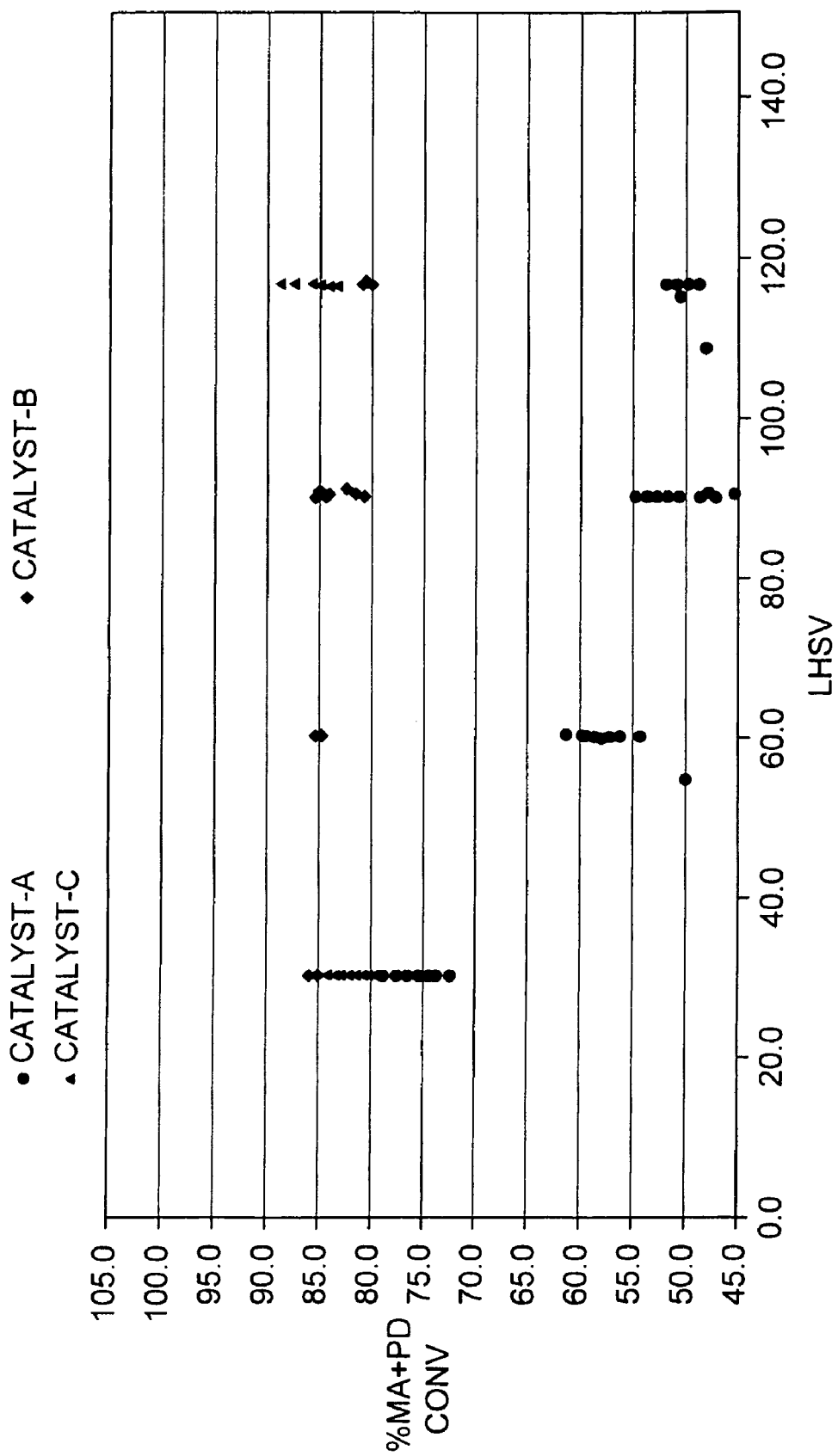
FIG. 3 is a plot of the activity for methyl acetylene and propadiene conversion to propylene versus LHSV.
Figure 4:
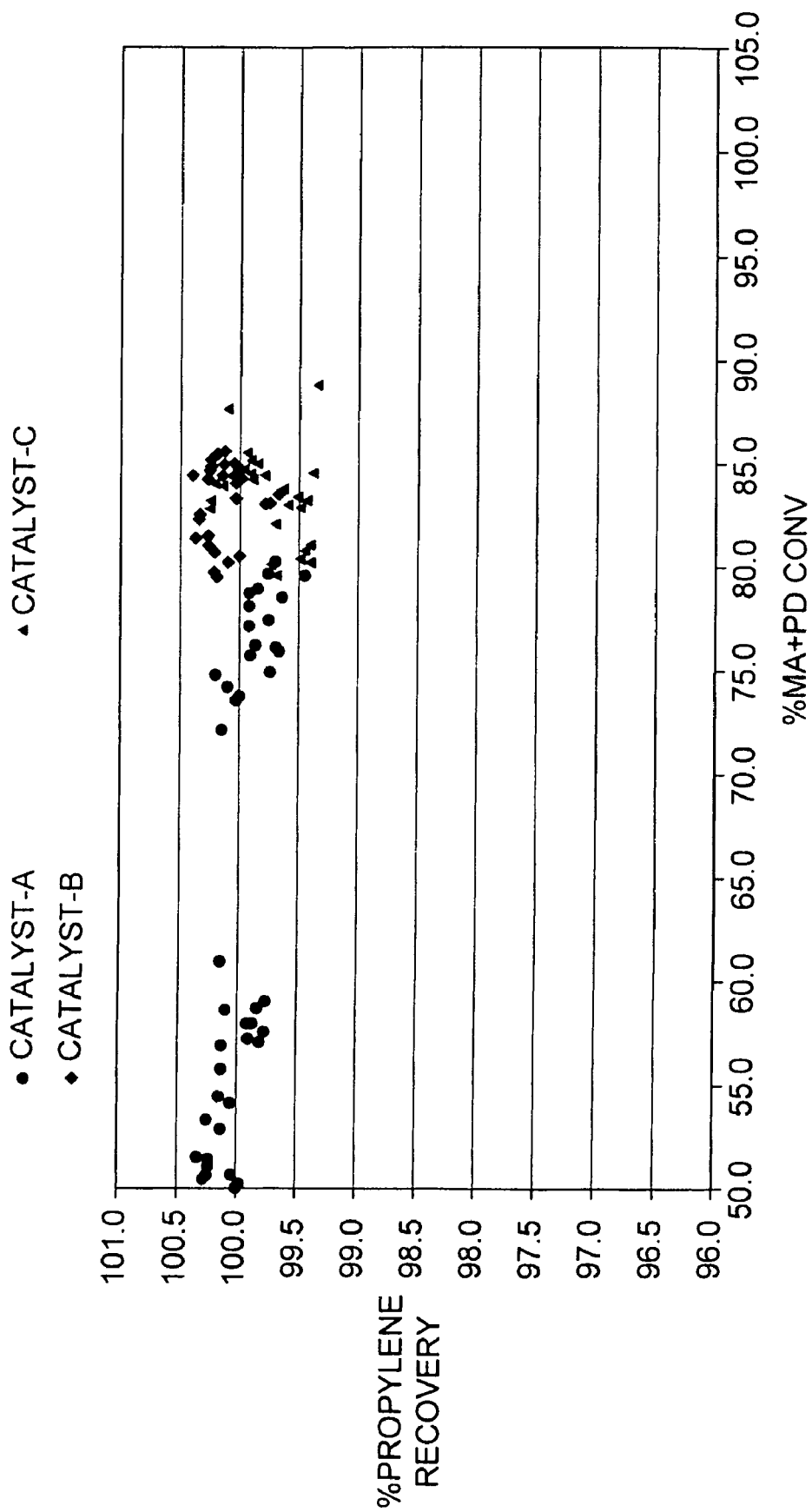
FIG. 4 is a plot of the selectivity for propylene recovery in percent versus methyl acetylene and propadiene conversion.

The performance of these three catalysts is compared for the selective hydrogenation of MAPD and is shown in FIGS. 3 and 4. The catalysts all have nominally the same bulk Pd composition. The feed composition had 1300 wt. ppm MA and 300 wt. ppm PD, 65/35 C3/C3=. The reaction conditions were 3550 kPa (500 psig) with a hydrogen to MAPD molar ratio of 1.2. The catalyst bed temperature was 40° C. The results shown in FIG. 3 indicate that Catalyst B is more active than Catalyst A, and that Catalyst C is even more active than Catalyst B. The propylene recovery is shown as a function of MAPD conversion in FIG. 4. Catalysts A and B have similar selectivities at the higher conversion, while Catalyst C has the best selectivity at the higher conversion. The differences, although nominally the same bulk conditions, point to the importance of the ratios of the metals deposited on the outer layer.

A second set of catalysts were formed and tested. These catalysts comprised a palladium on alumina formulation only for differing Pd:Al atomic ratios. Catalyst D comprised a layered sphere with an inner core of cordierite with a 3 mm diameter, and a 25 micrometer outer layer of γ-alumina ($Al_2O_3$). The metals deposited on the outer layer were 0.02 wt % Pd, and 0.33 wt % K on the bulk basis. The theoretical Pd:Al atomic in the layer is 0.002, and the catalyst was prepared with long evaporation procedure with acid.

A second catalyst, Catalyst E, comprised the same makeup as catalyst D, except the outer layer was a 50 micrometer outer layer of γ-alumina ($Al_2O_3$). The theoretical Pd:Al atomic in the layer is 0.001.

A third catalyst, Catalyst F, comprised a layered sphere with an inner core of cordierite with a 3 mm diameter, and a 25 micrometer outer layer of γ-alumina ($Al_2O_3$). The metals deposited on the outer layer were 0.05 wt % Pd, and 0.33 wt % K on the bulk basis. The theoretical Pd:Al atomic in the layer is 0.005, and the catalyst was prepared with long evaporation procedure with acid.

A fourth catalyst, Catalyst G, was a commercially available catalyst with 0.1 wt % Pd on γ-alumina on a 0.1" diameter sphere (2.54 mm).

Figure 5:
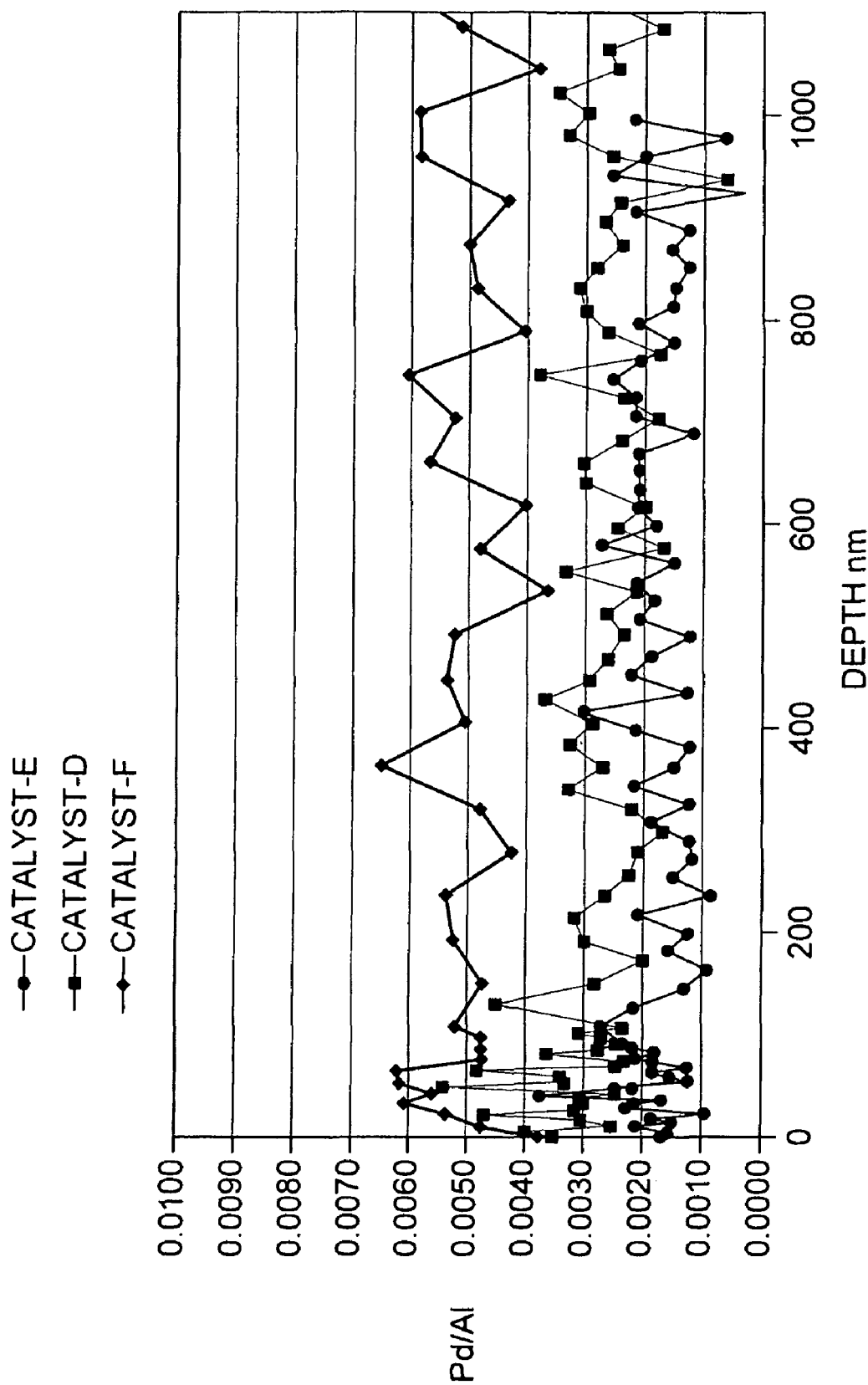
FIG. 5 is a plot of the palladium to aluminum layer profiles for palladium only catalysts.

The Pd:Al ratio profiles, shown in FIG. 5, for the catalysts were taken with XPS sputtering. Catalyst D was designed with a 25 micrometer layer to achieve a measured Pd:Al ratio of 0.002. Catalyst E, due to surface enrichment has a Pd:Al atomic ratio of 0.002, which is twice its theoretical value according to the Catalyst E bulk composition. Catalyst F has a Pd:Al atomic ratio of 2.5 times the ratio of Catalyst D, due to the higher Pd loading. Catalyst G has a Pd loading of 1000 wt ppm and is considered a state-of-the-art catalyst for this application.

Figure 6:
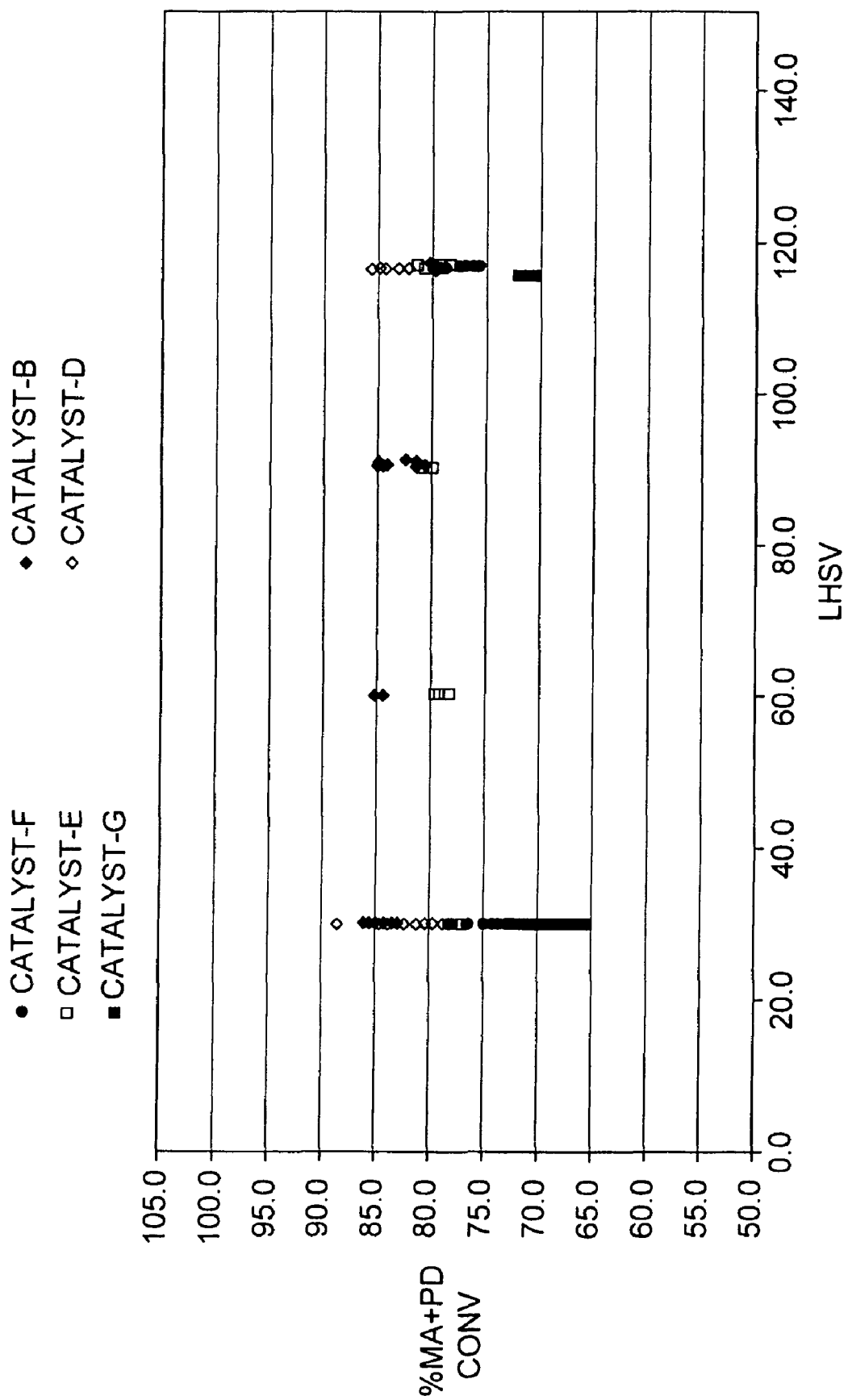
FIG. 6 is a plot of the activity for methyl acetylene and propadiene conversion to propylene versus LHSV.
Figure 7:
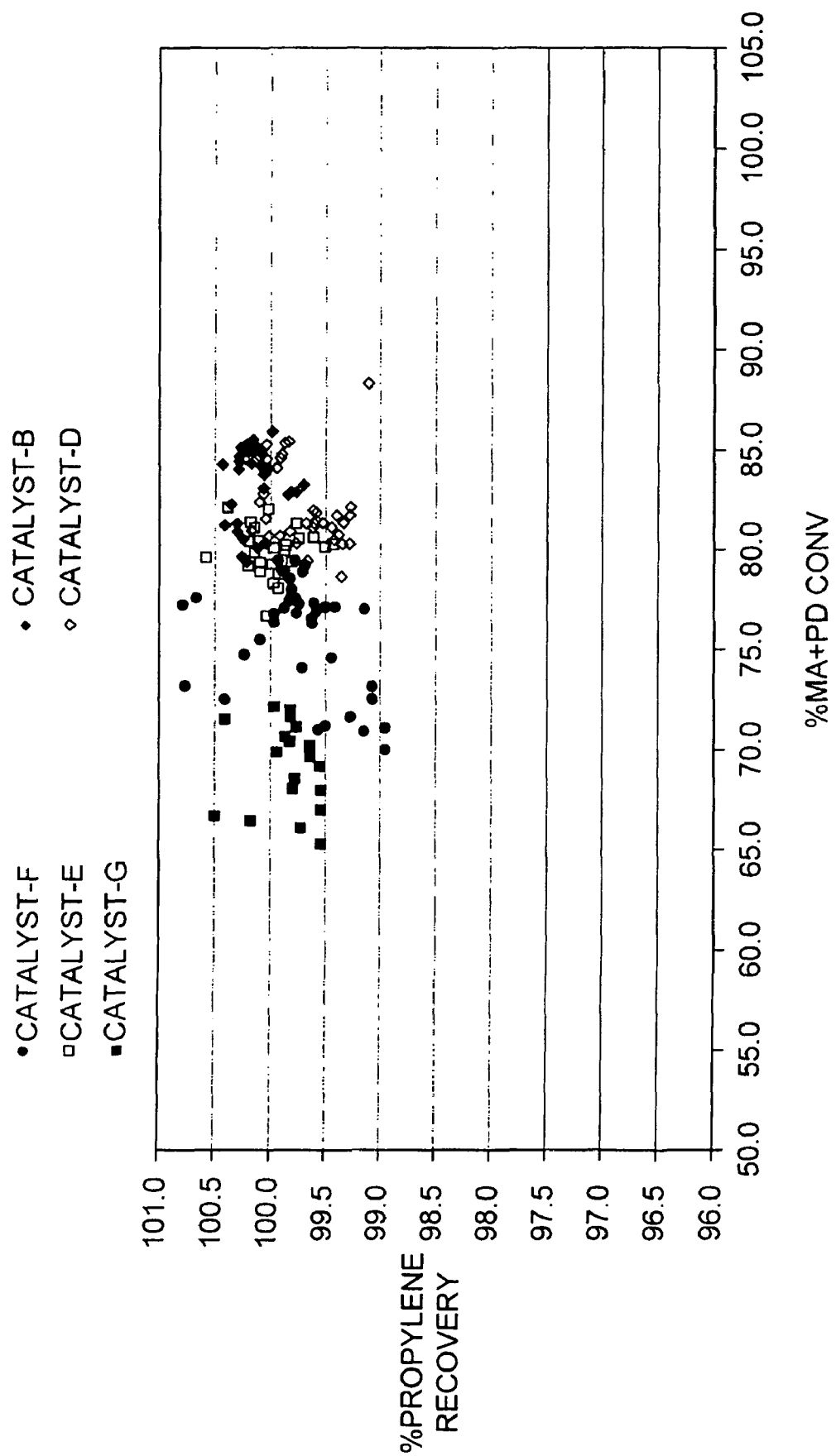
FIG. 7 is a plot of the selectivity for propylene recovery in percent versus methyl acetylene and propadiene conversion.

The performance of these four catalysts, along with Catalyst B, is compared for the selective hydrogenation of MAPD and is shown in FIGS. 6 and 7. The feed composition had 1300 wt. ppm MA and 300 wt. ppm PD, 65/35 C3/C3=. The reaction conditions were 3550 kPa (500 psig) with a hydrogen to MAPD molar ratio of 1.2. The catalyst bed temperature was 40° C. The results shown in FIG. 6 indicate that Catalyst D has the best activity among Catalysts D, E, F and G. The propylene recovery is shown as a function of MAPD conversion in FIG. 7. Catalyst D also has the best selectivity among the Catalysts D, E, F and G with the Pd only formulation. Furthermore FIG. 7 shows that Catalyst D has comparable selectivity to the Pd/Cu formulation of Catalyst B. Catalyst F has a higher Pd loading, but is less active than Catalyst D. This suggests that the optimum Pd:Al ratio is below that of Catalyst F at 0.005. Catalyst G, which is a commercial catalyst and has about twice the loading of Catalyst F, has activity drop even more than Catalyst F.

Figure 8:
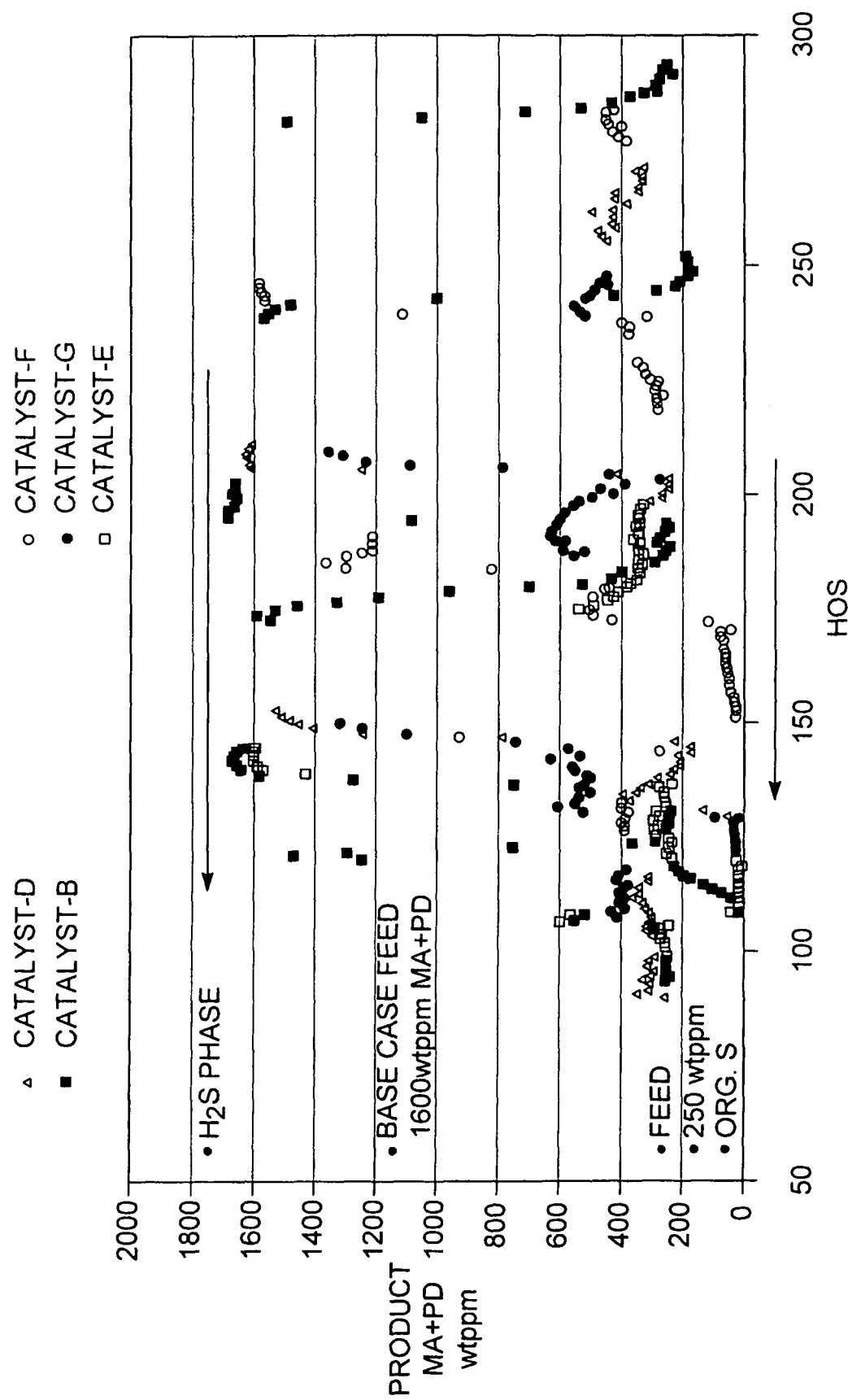
FIG. 8 is a plot of the organic and H2S sulfur recoveries.

A further test included the sulfur recovery behavior of the catalysts. Sulfur was introduced in the form of $H_2S$ at approximately 3 wt. ppm sulfur in the reactor feed. The $H_2S$ was introduced in the gas phase along with hydrogen. The gas was mixed with the liquid feed before the reactor inlet as the combined feed. The liquid phase feed comprised 1300 wt ppm MA and 300 wt ppm PD. Sulfur was also introduced as organic sulfur via the liquid phase feed. In the liquid phase, the organic sulfur phase used iso-butyl-mercaptan and thiophene with an equivalent total sulfur contribution of 1 wt. ppm each in the liquid feed. The liquid phase feed comprised a 200 wt. ppm MA and a 50 wt. ppm PD. The results are shown in FIG. 8 which shows the sulfur recovery behavior. Although all the catalysts showed some loss of activity in the presence of $H_2S$, Catalyst D maintained activity during the organic sulfur tests and also recovered its activity better than Catalyst G from the $H_2S$ phase.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A catalyst for selective hydrogenation comprising:
   a layered structure having an inner core comprising an inert material;
   an outer layer bonded to the inner core, comprising aluminum oxide and a metal oxide selected from the group consisting of gamma alumina, delta alumina, eta alumina, theta alumina, silica-alumina, zeolites, non-zeolitic molecular sieves, titania, zirconia, and mixtures thereof;
   a first metal deposited on the outer layer, wherein the first metal is selected from a first group consisting an IUPAC Group 8-10 metal, and mixtures thereof; and
   a second metal deposited on the outer layer, wherein the second metal is selected from a second group consisting of an IUPAC Group 11-17 metal, and mixtures thereof;
   wherein the atomic ratio of the first metal to the aluminum in the outer layer is in a ratio between 0.001 and 0.005, wherein the atomic ratio of the second metal to the first metal is less than 6.

2. The catalyst of claim 1 further comprising a third metal deposited on the outer layer, wherein the third metal comprises a metal selected from the group consisting of an IUPAC Group 1-2 metal, and mixtures thereof.

3. The catalyst of claim 2 wherein the third metal is selected from the group consisting of potassium or lithium.

4. The catalyst of claim 1 wherein the first metal is palladium or platinum.

5. The catalyst of claim 1 wherein the second metal is selected from the group consisting of copper, silver, gold, tin, germanium, lead, and mixtures thereof.

6. The catalyst of claim 1 wherein the atomic ratio of the second metal to the first metal is less than 1.5.

7. The catalyst of claim 1 wherein the inner core comprises a solid material selected from the group consisting of cordierite, mullite, olivine, zirconia, spinel, kyanite, aluminas, silicas, aluminates, silicates, titania, nitrides, carbides, borosilicates, boria, aluminum silicates, magnesia, fosterite, kaolin, kaolinite, montmorillonite, saponite, bentonite, clays that have little or low acidic activity, gamma alumina, delta alumina, eta alumina, theta alumina and mixtures thereof.

8. The catalyst of claim 1 wherein the inner core has an effective diameter from 0.05 mm to 10 mm.

9. The catalyst of claim 1 wherein the outer layer has an effective thickness between 1 micrometers and 200 micrometers.

10. The catalyst of claim 9 wherein the outer layer has an effective thickness between 20 and 70 micrometers.

11. The catalyst of claim 1 wherein the metal oxide is a silica-alumina molecular sieve.

12. The catalyst of claim 1 wherein the metal oxide is gamma-alumina.

13. The catalyst of claim 1 wherein the metal oxide is theta-alumina.

14. The catalyst of claim 1 further comprising a modifier metal, wherein the metal is selected from the group consisting of an IUPAC Group 6-7 metal and mixtures thereof.

15. The catalyst of claim 14 wherein the modifier metal is selected from the group consisting of molybdenum, tungsten, rhenium, and mixtures thereof.

16. A catalyst for selective hydrogenation comprising:
    a layered structure having an inner core comprising an inert material;
    an outer layer bonded to the inner core, and comprising an alumina;
    a first metal deposited on the outer layer, wherein the first metal is palladium; and
    a second metal deposited on the outer layer, wherein the second metal is copper;
    wherein the atomic ratio of the first metal to the aluminum in the outer layer is in a ratio between 0.001 and 0.005, wherein the atomic ratio of the second metal to the first metal is less than 6.

17. The catalyst of claim 16 wherein the atomic ratio of the second metal to the first metal is less than 1.5.

18. The catalyst of claim 16 wherein the inner core has an effective diameter from 0.05 mm to 10 mm.

19. The catalyst of claim 16 wherein the outer layer has an effective thickness between 1 micrometers and 200 micrometers.

* * * * *